_US005753443A_

United States Patent [19]
Barbesti

[11] Patent Number: 5,753,443
[45] Date of Patent: May 19, 1998

[54] CRYSTALLIZED FORMULATION FOR STAINING DNA, ITS PREPARATION AND KIT

[75] Inventor: Silvia Barbesti, Milan, Italy

[73] Assignee: BIO-RAD Laboratories S.r.l., Segrate, Italy

[21] Appl. No.: 648,048

[22] PCT Filed: Sep. 24, 1994

[86] PCT No.: PCT/EP94/03217

§ 371 Date: May 10, 1996

§ 102(e) Date: May 10, 1996

[87] PCT Pub. No.: WO96/09529

PCT Pub. Date: Mar. 28, 1996

[51] Int. Cl.$^6$ .............. C12N 1/68; C12N 9/96; G01N 33/567; G01N 33/00
[52] U.S. Cl. .............. 435/6; 435/21; 435/188; 436/94
[58] Field of Search .............. 435/6, 23, 7.1, 435/40.5, 40.51, 810, 21, 188; 436/501, 800, 63, 94

[56] References Cited

U.S. PATENT DOCUMENTS

| | | | |
|---|---|---|---|
| 4,087,328 | 5/1978 | Swaisgood | 435/176 |
| 4,668,618 | 5/1987 | Thornthwaite | 435/6 |

OTHER PUBLICATIONS

Barbesti et al. "DNA Flow Cytometry Performed By Stablized Propidium Iodide Staining," *European Journal of Histochemistry*, vol. 37, 1993, p. 68.

Brown et al. "Propellant–driven aerosols of functional proteins as potential therapeutic agents in the respiratory tract," *Immunopharmacology*, vol. 28, No. 3, Oct. 1994, pp. 241–257.

Luisi et al. "Reverse micelles as hosts for proteins and small molecules", *Biochimica & Biophysica Acia* 947 (1988) pp. 209–246.

1996 Biochemcals Catalog. (Boehringer Mannheim: Indianapolis, IN) p. 495, 1996.

van der Engh et al. Cytometry (1984) vol. 5, pp. 108–117 1984.

*Primary Examiner*—Jon P. Weber
*Assistant Examiner*—Susan Hanley
*Attorney, Agent, or Firm*—Darby & Darby

[57] ABSTRACT

A process is disclosed for making a crystallized formulation for staining nuclear DNA to be used in flow cytometery. The crystallized DNA staining formulation and a kit containing the crystallized DNA staining formulation are provided. The staining formulation contains a mixture of a dye, a ribonuclease and a non-ionic hydrophilic surfactant. The process for preparing the formulation comprises mixing the dye, the enzyme and the surfactant and evaporating the mixture under vacuum to form a crystallized residue. The kit comprises the crystallized DNA staining formulation packed in single dose vials, each vial being sufficient for one analytic determination. Optionally, the kit may contain additional vials comprising a diluent used to reconstitute the crystallized residue at the time of use.

10 Claims, No Drawings

CRYSTALLIZED FORMULATION FOR STAINING DNA, ITS PREPARATION AND KIT

This application is the U.S. National Phase of international application No. PCT/EP94/03217, filed Sep. 24, 1994, and designating the Unites States.

The present invention relates to a process for the production of a preparation for staining nuclear DNA to be used in flow cytometry, the preparation obtained by such a process, and a kit for its use.

It is well known that cytofluorometric analysis took a fundamental role in diagnostics and its use is steadily increasing, together with the development of new and more sophisticated analysis techniques and apparatus.

More particularly, the determination of cellular DNA contents through flow cytometry is fundamental in the oncologic field as well as in determining the cellular ploidy by cytofluorometric analysis.

Up to now the working solution containing the specific dye and a thermolabile enzyme, was prepared in an extemporaneous way at the time of using it, because of the well known stability problems of the proteins in the anhydrous condition, but such a process is not at all satisfactory because it is also well known that extemporaneous preparations depend too much from the present situation and the operator's skill, thus they do not warrant reproducible results.

Indeed, as proteins in the anhydrous condition generally show stability problems and their rehydration is rather long, difficult and sometimes incomplete, it was hitherto considered impossible to make a preparation for staining nuclear DNA to be stored in the anhydrous condition and to be reconstructed at the time of use.

It was now surprisingly found that this problem is brilliantly solved by mixing the protein with a surfactant, so as to cause the formation of a water envelope around the molecule, obtain a better stability with time and a more complete hydration at the moment of use.

In other words, not a true lyophilization but instead a crystallization of the preparation is carried out, so that it may be perfectly stored for a long time.

The ingredients to be used in the production of the preparation according to the present invention must be chosen obviously in a proper way. As enzyme a specific ribonuclease is used, for instance type A bovine ribonuclease; as a dye, a fluorescent halide binding specifically to nucleic acids, preferably propidium iodide, but other fluorescent halides are suitable as well; as a surfactant, it is necessary to use a non ionic surfactant such as NONIDET P 40 (BDH Laboratory Supplies Ltd., Poole, Dorset, Great Britain). NONIDET P40 is (octylphenoxyl) polyethoxyethanol.

Once the working solution is prepared, it is delivered in vials in such amount as to allow an analytic determination for each vial, which is therefore single dose, and the solution water is evaporated under vacuum.

It is known that DNA staining may take place either in a hypotonic medium, if it is desired to stain only isolated nuclei, or in an isotonic medium, if it desired to keep intact the cell structure for possible morphologic studies or checking proliferation markers.

Two different diluents are therefore prepared for reconstituting the working solution, consisting of salts with a different concentration according to either diluent.

Consequently, three different single dose kits may be supplied to users, namely the vial containing the preparation, accompanied by a bottle containing either the isotonic or the hypotonic diluent, or two vials each with one of the diluents.

The production of the preparation according to the present invention will be now illustrated in detail in the following practical example of preparation, which however should not be construed as limiting in any way the scope of the invention.

EXAMPLE

The chosen dye is propidium iodide, that links specifically by intercalation to the nucleic acids in their double strand structure; it is therefore necessary to remove the cell RNA by enzymatic digestion, using a specific ribonuclease, so as to avoid an overestimation (moreover the RNA contents of a cell is not constant, but it may vary with the state of activity).

Access of the dye to the nuclear compartment is made easier by using a surfactant, present at a low concentration, which makes the nuclear membrane permeable.

Firstly a high concentration stock solution of propidium iodide is prepared, dissolving 500 µg/ml of the dye in twice distilled water. The mixture so obtained is left standing on a magnetic agitator for at least 4–6 hours so as to obtain the complete dissolution of the dye. The solution is then filtered with a membrane of cellulose acetate with a pore size 0.22 µ so as to remove possible insoluble residues. Subsequently the working solution is prepared: to one part of stock solution, 9 parts of twice distilled water are added (the final concentration of the dye results to be 50 µg/ml), 1 mg/ml of crystallized bovine ribonuclease type A and 0.1% v/v NONIDET P 40. The mixture is again placed on a magnetic agitator for at least 2 hours, adjusting the magnet speed so as not to create foam, and then filtered with a membrane of cellulose acetate with a pore size 0.22 µ. The working solution is delivered in conic bottom test tubes having a capacity of 1.5 ml, in a quantity of 1 ml for each tube. Water evaporation is obtained using a thickener with a fixed angle rotor, with a low speed centrifugation (1500 rpm) for 8 hours at controlled temperature (25° C.) under vacuum. At the end the test tubes are closed with a proper pressure stopper.

Two different diluents are then prepared for the reconstitution of the working solution. Isotonic diluent No. 1:0.155M NaCl, 15 mM $NaN_3$ in twice distilled water. Hypotonic diluent No. 2:0.01M NaCl, 15 mM $NaN_3$ in twice distilled water. Both solution, after complete dissolution on magnetic agitator, are filtered with a membrane of cellulose acetate with a pore size of 0.22 µ for removing possible insoluble residues and sterilization from bacterial contaminants.

I claim:

1. A process for preparing a crystallized formulation for staining nuclear DNA, comprising a DNA specific dye, a non-ionic hydrophilic surfactant and a ribonuclease, comprising the steps of:
   (a) mixing said ribonuclease with the surfactant and the DNA specific dye; and
   (b) evaporating the resulting mixture under vacuum to form a crystallized residue that may be reconstituted at the moment of use with a diluent.

2. The process of claim 1, wherein the DNA specific dye is a fluorescent halide.

3. The process of claim 2, wherein the fluorescent halide is propidium iodide.

4. The process of claim 1, wherein the non-ionic hydrophilic surfactant is (octylphenoxyl)polyethoxyethanol.

5. The process of claim 1, wherein the ribonuclease is bovine ribonuclease type A.

6. The process of claim 1, wherein the diluent for the reconstitution at the moment of use is a hypotonic or isotonic medium.

7. A formulation for staining nuclear DNA, comprising a crystallized residue comprising a DNA specific dye, a ribonuclease and a non-ionic hydrophilic surfactant, which may be reconstituted at the moment of use with a hypotonic or isotonic medium.

8. A crystallized formulation for staining nuclear DNA comprising a DNA specific dye, a non-ionic hydrophillic surfactant and a ribonuclease, made by a process comprising the steps:

(a) mixing said ribonuclease with the surfactant and the DNA specific dye; and (b) evaporating the resulting mixture under vacuum to form a crystallized residue.

9. The formulation for staining nuclear DNA according to claim 7 wherein said formulation is packed in single containers sufficient for only one analytic determination per each container.

10. A kit comprising a formulation for staining nuclear DNA, comprising:

(a) a crystallized residue comprising a DNA specific dye, a non-ionic hydrophilic surfactant and a ribonuclease wherein said formulation is packaged in a single dose container sufficient for only one analytic determination per each container, and (b) either (i) a container containing an isotonic or a hypotonic diluent; or (ii) a first container containing an isotonic diluent and a second container containing a hypotonic diluent.

\* \* \* \* \*